United States Patent
Erskine

(10) Patent No.: US 10,001,461 B2
(45) Date of Patent: Jun. 19, 2018

(54) SENSOR SELF-TEST

(71) Applicant: AKTIEBOLAGET SKF, Göteborg (SE)

(72) Inventor: Joseph Erskine, Falkirk (GB)

(73) Assignee: AKTIEBOLAGET SKF, Gothenburg (SE)

( * ) Notice: Subject to any disclaimer, the term of this patent is extended or adjusted under 35 U.S.C. 154(b) by 202 days.

(21) Appl. No.: 14/777,754

(22) PCT Filed: Mar. 18, 2013

(86) PCT No.: PCT/EP2013/055570
§ 371 (c)(1),
(2) Date: Sep. 17, 2015

(87) PCT Pub. No.: WO2014/146680
PCT Pub. Date: Sep. 25, 2014

(65) Prior Publication Data
US 2016/0054271 A1 Feb. 25, 2016

(51) Int. Cl.
*G01N 29/30* (2006.01)
*G01M 13/04* (2006.01)
*G01N 29/14* (2006.01)
*G01N 29/34* (2006.01)
*G01N 29/36* (2006.01)

(52) U.S. Cl.
CPC .......... *G01N 29/30* (2013.01); *G01M 13/045* (2013.01); *G01N 29/14* (2013.01); *G01N 29/34* (2013.01); *G01N 29/36* (2013.01); *G01N 2291/2696* (2013.01)

(58) Field of Classification Search
CPC ........ G01N 29/30; G01N 29/14; G01N 29/34; G01N 29/36; G01M 13/045
USPC ......................................................... 73/1.82
See application file for complete search history.

(56) References Cited

U.S. PATENT DOCUMENTS

| | | | | |
|---|---|---|---|---|
| 5,437,178 A | * | 8/1995 | Esin | ...................... G01F 23/296 367/7 |
| 5,852,793 A | * | 12/1998 | Board | ..................... G01H 1/003 702/183 |
| 2004/0050163 A1 | | 3/2004 | Komninos | |

(Continued)

*Primary Examiner* — Lisa Caputo
*Assistant Examiner* — Tarun Sinha
(74) *Attorney, Agent, or Firm* — Bryan Peckjian; SKF USA Inc. Patent Dept

(57) ABSTRACT

A crystal self-test circuit is used to self-test either an acoustic emission crystal or a vibration crystal installed onto one of a bearing, a bearing housing, and a machine. A crystal self-test circuit includes a multiplexer IC, which toggles between a pulse injection configuration and a signal collection configuration. In the pulse injection configuration, the multiplexer IC provides signal communication between a crystal self-test input and the sensing emission crystal. In the signal collection configuration, the multiplexer IC provides signal communication between the sensing emission crystal and a signal analyzer. In operation, the multiplexer IC applies a waveform (preferably a square wave) to the sensing emission crystal over a predetermined time period. The multiplexer IC then toggles to collect the output waveform from the sensing emission crystal and forwards the output waveform to the signal analyzer. The output signal can be amplified by a signal amplifier.

12 Claims, 11 Drawing Sheets

(56) References Cited

U.S. PATENT DOCUMENTS

2007/0074571 A1    4/2007  Haynes et al.
2013/0166227 A1*  6/2013  Hermann ............... G01N 29/30
                                                             702/51

* cited by examiner

SENSOR SELF-TEST

CROSS REFERENCE TO RELATED APPLICATION

This is a United States National Stage Application claiming the benefit of International Application Number PCT/EP2013/055570 filed on 18 Mar. 2013 (18.03.2013), which is incorporated herein by reference in its entirety.

BACKGROUND OF THE INVENTION

Technical Field of the Invention

The present invention relates to an apparatus and method for testing an acoustic emission (AE) piezoelectric crystal and a vibrational crystal without the need for a separate external signal source or stimulation being applied to a bearing, a bearing housing, or a general machine enclosure.

Background Art

Acoustic emission (AE) piezoelectric crystals and vibration crystals are secured directly to one of a bearing, a bearing housing, or the associated machine. In order to ensure that the acoustic emission (AE) piezoelectric crystals and vibration crystals are properly secured in position, an external signal was applied using a separate sensor or secondary acoustic emission (AE) piezoelectric crystal with a signal generator. An alternative method to determine if the acoustic emission (AE) piezoelectric crystal is properly secured in position would be to excite the bearing by tapping the bearing with a metallic object. These solutions require the use of additional components, additional set up equipment, and necessitates extra time.

What is desired is a system and respective method of use for reducing additional components and/or equipment to verify proper installation of an acoustic emission (AE) piezoelectric crystal upon a bearing, a bearing housing, or an associated machine.

DISCLOSURE OF THE INVENTION

The present invention is directed towards an apparatus and respective method for testing an acoustic emission crystal and a respective attachment of the acoustic emission crystal to an object, such as a bearing, a bearing housing, or a machine housing.

In a first aspect of the present invention, a self-test circuit for testing an acoustic emissions crystal comprising:
   a voltage source;
   a ground;
   a controller;
   a pulse waveform input;
   an analyzer; and
   a multiplexer IC having:
   a voltage input pin provided in signal communication with said ground,
   a ground pin provided in signal communication with said ground,
   a controller input pin provided in signal communication with said controller,
   a normally open pin provided in signal communication with said pulse waveform input,
   a common pin provided in signal communication with said acoustic emissions crystal;
   a normally closed pin output in signal communication with said analyzer, wherein in operation:
   said pulse waveform input provides a waveform to said multiplexer IC,
   the controller configures said multiplexer IC to pass said waveform to said acoustic emissions crystal, wherein said waveform is provided in signal communication with said acoustic emissions crystal,
   the waveform excites said acoustic emissions crystal, and
   the controller configures said multiplexer to pass said waveform emitted from said acoustic emissions crystal to said analyzer.

In a second aspect, the circuit further includes an acoustic emission crystal acquired signal amplifier, wherein said acoustic emission crystal acquired signal amplifier is integrated between said normally closed pin and said analyzer.

In another aspect, the sealing system provides for tolerance compensation along a radial direction.

In another aspect, the waveform is provided in a square waveform factor.

In a method aspect of the present invention, a self-test circuit provides a method of testing an acoustic emissions crystal, the method comprising steps of:
   configuring a circuit controller into a pulse injection configuration, placing a signal generation source in signal communication with said acoustic emissions crystal;
   injecting a waveform into said acoustic emissions crystal;
   configuring said circuit controller into a signal collection configuration, placing a signal generation source in signal communication with a signal analyzer;
   obtaining a waveform output from said acoustic emissions crystal; and
   providing said waveform output to a signal analyzer.

One advantage of the present invention is the ability to test an acoustic emission crystal that has been correctly fastened to a bearing, a bearing housing, or a general machine enclosure exclusive of a second separate sensor or secondary acoustic emission (AE) piezoelectric crystal. The circuit applies a repeatable testing signal to the acoustic emission crystal to validate the acceptable installation and function thereof. The process can be characterized by adjusting a time prior for injection of an input signal to the subject acoustic emission (AE) piezoelectric crystal.

These and other features, aspects, and advantages of the invention will be further understood and appreciated by those skilled in the art by reference to the following written specification, claims and appended drawings, which follow.

BRIEF DESCRIPTION OF THE DRAWINGS

For a fuller understanding of the nature of the present invention, reference should be made to the accompanying drawings in which.

Like reference numerals refer to like parts throughout the several views of the drawings.

MODES FOR CARRYING OUT THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as normally oriented and described herein. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
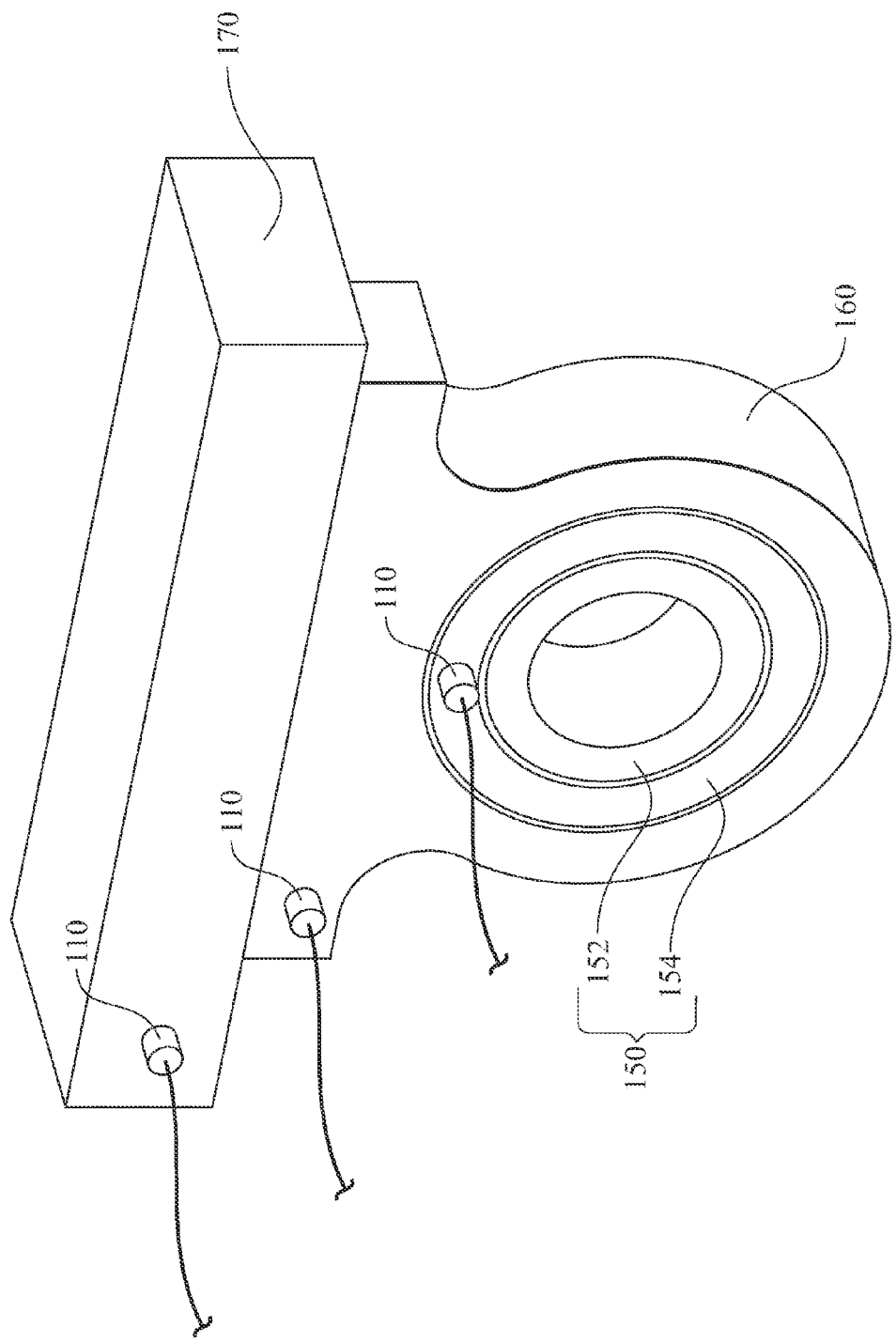
FIG. 1 presents an isometric view of an acoustic emissions crystal connected to a bearing, a bearing housing, and a general machine enclosure.

Acoustic emission crystals 110 (or alternatively referred to as SEE piezoelectric crystals) are coupled to one of a bearing 150, a bearing housing 152, and a general machine 154 to monitor the operational condition of the apparatus as illustrated in FIG. 1. The acoustic emission crystal 110 would be coupled to a fixed portion of the bearing 150. In the exemplary embodiment, a bearing outer ring 152 is fixed and a bearing inner ring 154 rotates. In this configuration, the acoustic emission crystals 110 would be affixed to the bearing outer ring 154. Alternatively, in a configuration where the inner ring 152 is fixed, the acoustic emission crystals 110 would be affixed to the bearing inner ring 152. The current installation validation process requires installation of a second crystal or other exciting device to provide an exciting signal to the subject acoustic emission crystal 110. An acoustic emissions crystal self-test circuit 100, as presented in FIG. 2, provides a solution to eliminate the need for installation of the second crystal.

Figure 2:
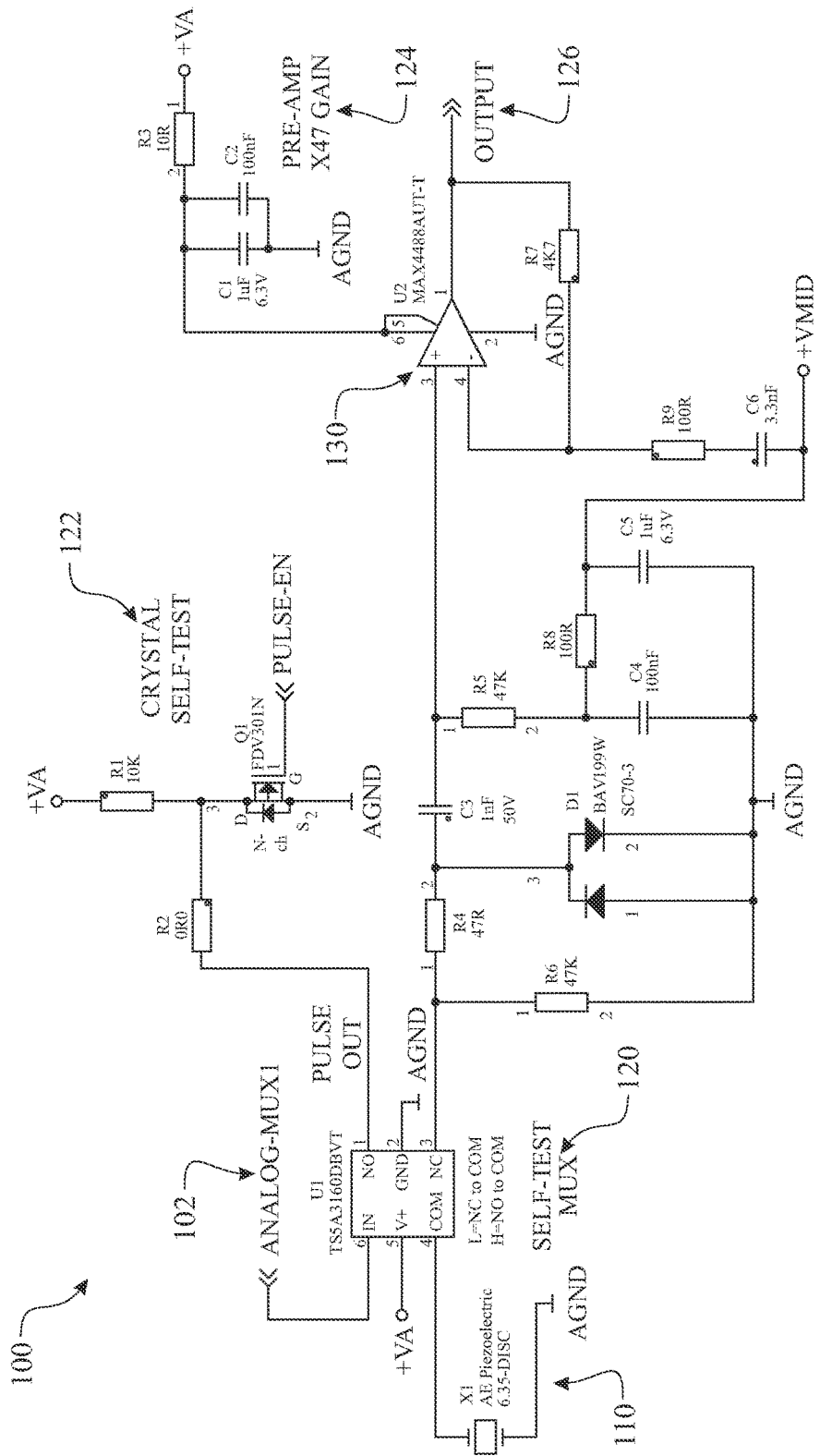
FIG. 2 presents an electrical schematic of an exemplary acoustic emissions crystal self-test circuit.

An acoustic emissions crystal self-test circuit 100 is presented in FIG. 2. The acoustic emissions crystal self-test circuit 100 provides a self-test process to an acoustic emission crystal 110. The acoustic emission crystal 110 is secured to one of a bearing, a bearing housing, and a general machines enclosure prior to exercising the testing process. The acoustic emissions crystal self-test circuit 100 provides an input for exciting the acoustic emission crystal 110 exclusive of a requirement of installation of a second crystal.

The acoustic emissions crystal self-test circuit 100 includes a multiplexer IC 120 (also referenced by circuit component reference U1), which toggles between a square wave application or signal injection configuration to an acoustic emission crystal 110 and a signal collection configuration from the acoustic emission crystal 110. The preferred multiplexer IC 120 includes six (6) electrical connections. A power source or voltage is provided in electrical communication with a voltage input pin, referenced as V+. A ground (AGND) completes the power source and is provided in electrical communication with a ground pin (GND) of the multiplexer IC 120.

The state or configuration of the multiplexer IC 120 is controlled by an external source or circuit controller 102, referred to as an ANALOG-MUX1 provided to the input or controller pin (IN) of the multiplexer IC 120. The ANALOG-MUX1 is preferably provided by a computer-operated controller 102. The multiplexer IC 120 is initially placed into a pulse injection configuration, placing a normally open (NO) pin and a common (COM) pin of the multiplexer IC 120 in signal communication. A pulse is supplied to the multiplexer IC 120 from a crystal self-test input 122, wherein the pulse is provided in signal communication with the normally open (NO) pin of the multiplexer IC 120. The pulse is preferably provided in a square waveform. The acoustic emission crystal 110 is provided in signal communication with the common (COM) pin of the multiplexer IC 120. The computer-operated controller would control the time in which the signal is provided from the crystal self-test input 122 to the acoustic emission crystal 110. It is understood that the pulse application time period can be optimized through calculations or experimentation, as will be described below. Once the desired pulse is applied to the acoustic emission crystal 110, the signal provided to the input or controller pin (IN) of the multiplexer IC 120 is changed, causing the configuration of the multiplexer IC 120 to convert to a signal collection configuration.

The signal collection configuration places a normally closed (NC) pin and a common (COM) pin of the multiplexer IC 120 in signal communication. The signal obtained from the acoustic emission crystal 110 is subsequently transferred to a signal output 126 (OUTPUT). The resulting amplified signal is preferably provided to the analytical tools as a signal output 126. The acoustic emissions crystal self-test circuit 100 can be enhanced with the inclusion of an acoustic emission crystal acquired signal amplifier 130 (also referenced by circuit component reference U2). The acoustic emission crystal acquired signal amplifier 130 would be integrated into the acoustic emissions crystal self-test circuit 100 between the normally open (NO) pin of the multiplexer IC 120 and the signal output '126. The acoustic emission crystal acquired signal amplifier 130 amplifies the signal output from the acoustic emission crystal 110.

The acoustic emissions crystal self-test circuit 100 includes a pre-amp gain 124, which provides a support signal (in a form of a voltage) into the acoustic emission crystal acquired signal amplifier 130.

The preferred circuit utilizes a series of surface mount components. The multiplexer IC 120 is provided by Texas Instruments under manufacturer part number TS5A3160DBVT and is provided in a six pin SOT-23-6 surface mount assembly package. The application is for an analog switch, toggling configurations between:
(1) a normally open condition obtaining a signal from pin 1 and connecting that signal to a common pin 4, and
(2) a normally closed condition obtaining a signal from common pin 4 and connecting that signal to pin 3.

An input pulse is provided by the crystal self-test input 122. The crystal self-test input 122 includes a digital FET, N-Channel logic level transistor. The exemplary digital FET, N-Channel logic level transistor is provided by Fairchild Semiconductor under manufacturer part number FDV301N and is provided in a three pin SOT-23 surface mount assembly package. The crystal self-test input 122 generates a square wave, which is directed to and applies an initial excitation to the acoustic emission crystal 110, when the multiplexer IC 120 is configured to apply the signal thereto.

The output from the acoustic emission crystal 110 is amplified by the acoustic emission crystal acquired signal amplifier 130. The exemplary acoustic emission crystal acquired signal amplifier 130 is provided by Maxim Integrated Products under manufacturer part number MAX4488AUT-T and is provided in a six-pin SOT-23-6 surface mount assembly package.

The circuit can include additional electrical components, including a variety of resistors, capacitors and diodes, each of the components being provided in their respective surface mount configurations. The acoustic emissions crystal self-test circuit 100 includes exemplary values for each of the supporting electrical components. The exemplary resistors are identified having circuit reference numbers initiating with the letter "R". The resistor values are presented adjacent to the electrical component reference identifier. The resistors are preferably sourced in 0402 size packaging, with alternative sizes also being available, such as 0603, and the like and/or in multi-resistor packages. The exemplary capacitors are identified having circuit reference numbers initiating with the letter "C". The capacitor values and maximum voltage levels are presented adjacent to the electrical component reference identifier. The capacitors are preferably sourced in 0402 size packaging, with alternative sizes also being available, such as 0603, and the like. The exemplary diode is identified having circuit reference number initiating with the letter "D".

The exemplary diode (or more specifically a rectifier) (circuit reference number D1) is provided by Zetex under manufacturer part number BAV199W-7 and is provided in a three-pin SOT-323 or three-pin SC70-3 surface mount assembly package.

Figure 3:
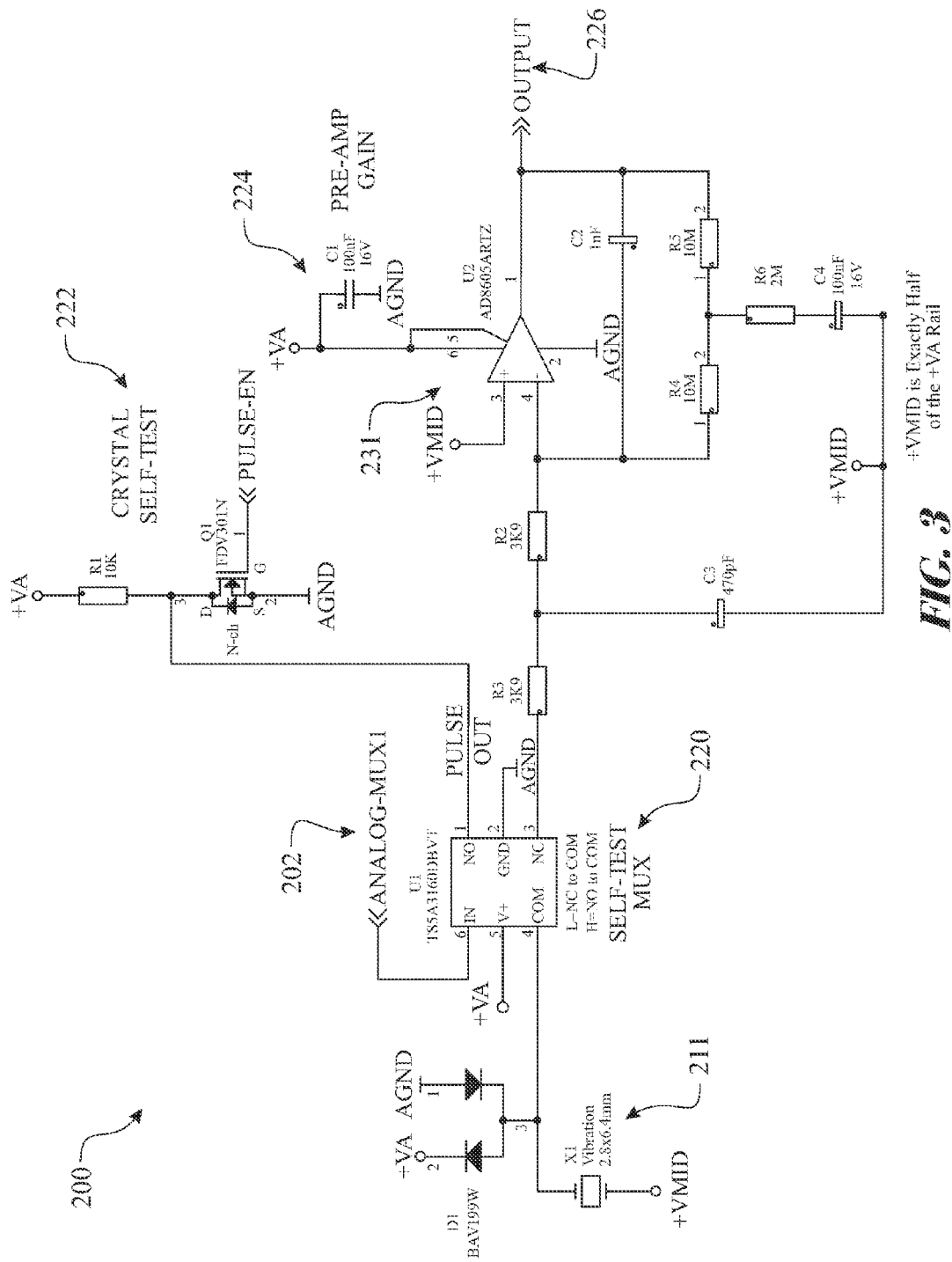
FIG. 3 presents an electrical schematic of an exemplary vibration crystal self-test circuit.

A second schematic illustrating an exemplary vibration crystal self-test circuit 200 is presented in FIG. 3. Although details of the vibration crystal self-test circuit 200 differ from those of the acoustic emissions crystal self-test circuit 100, the circuit generally comprises a majority of the same functional segments. Like functions of the vibration crystal self-test circuit 200 and the acoustic emissions crystal self-test circuit 100 are numbered the same except preceded by the numeral '2'. The vibration crystal self-test circuit 200 is engineered to excite and collect an output signal of a vibration crystal 211 (circuit reference number X1), whereas the acoustic emissions crystal self-test circuit 100 is engineered to excite and collect an output signal of the acoustic emission crystal 110. The vibration crystal acquired signal amplifier 231 (circuit reference number U2) utilizes a low noise complementary metal-oxide-semiconductor (CMOS) amplifier which is provided by Analog devices under manufacturer part number AD8605ARTZ, whereas the acoustic emission crystal acquired signal amplifier 130 utilizes Maxim Integrated Products under manufacturer part number MAX4488AUT-T. Like the acoustic emission crystal acquired signal amplifier 130, the exemplary vibration crystal acquired signal amplifier 231 is also provided in a six-pin SOT-23-6 surface mount assembly package. The overall functional operation of the vibration crystal self-test circuit 200 is similar to the acoustic emissions crystal self-test circuit 100 previously described. Essentially, the vibration crystal self-test circuit 200 includes a multiplexer IC 220 (circuit reference number U1), which toggles between a wave signal injection configuration, which applies a waveform (preferably a square wave) to the vibration crystal 211 and a signal collection configuration, which collects a waveform output from the vibration crystal 211. The output waveform is amplified by a pre-amp gain 224 and a vibration crystal acquired signal amplifier 230.

For unity, the acoustic emission crystal 110 and the vibration crystal 211 can collectively be referred to as sensing emission crystals 110, 211.

The circuit effectiveness was verified by testing the acoustic emissions crystal self-test circuit 100. Validation of the acoustic emissions crystal self-test circuit 100 was completed by testing the acoustic emission crystal 110 (more specifically an embedded SEE sensor) in a variety of configurations, with the results being presented in a series of charts presented in FIGS. 4 through 8.

Figure 4:
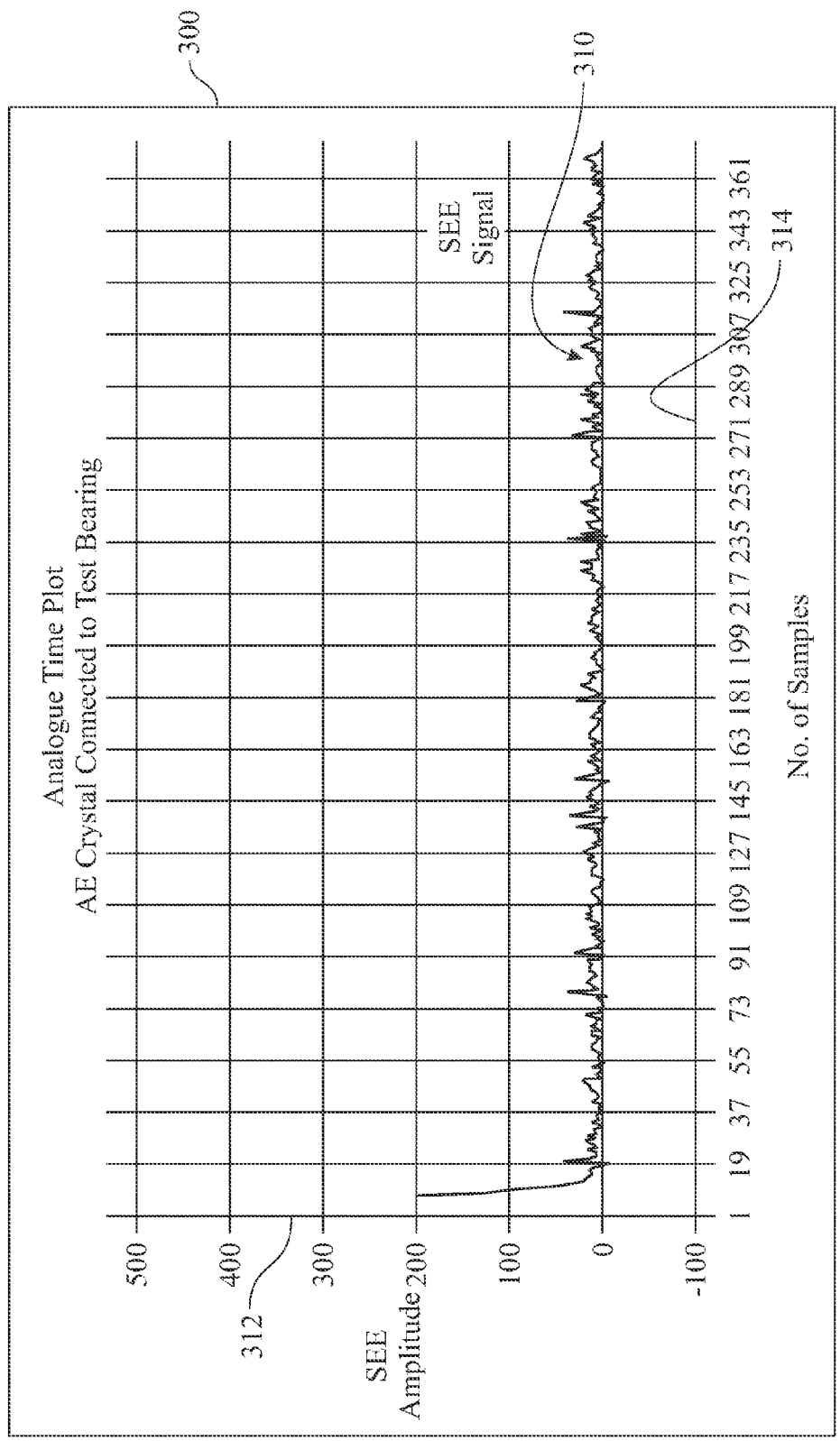
FIG. 4 presents an exemplary data chart illustrating an output signal of the SEE piezoelectric crystal, more specifically, an output amplitude of the SEE output signal over a period of ADC acquisitions (samples), wherein the data is obtained by the acoustic emissions crystal self-test circuit introduced in FIG. 1 and acoustic emissions crystal is connected to a test bearing.

In a first experiment, the acoustic emissions crystal self-test circuit 100 applied a single 10 us pulse to the acoustic emission crystal 110. The acoustic emission crystal 110 is coupled to a test bearing in accordance with a standard coupling or attachment procedure. The system recorded the output amplitude of each of a series of data points, wherein each data point was taken in conjunction with a linear time spatial relation. The data is measured, recorded and subsequently charted on an analogue time plot 300 as illustrated in FIG. 4. The analogue time plot 300 presents data along a sample number axis 312 and cross-referenced to an amplitude axis 314. The SEE sample 310 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude between 0 and 50.

Figure 5:
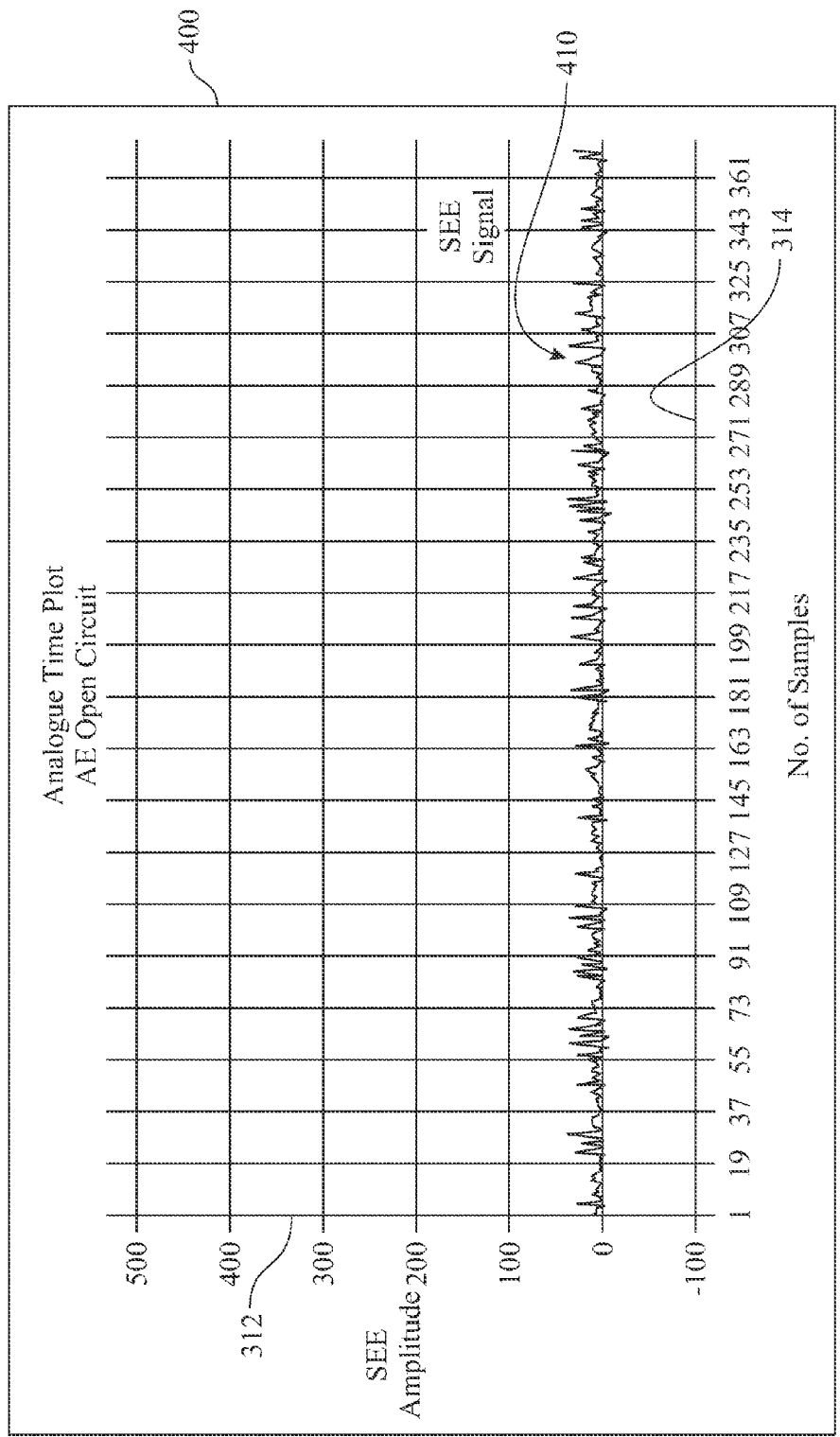
FIG. 5 presents an exemplary data chart illustrating an output signal of the SEE piezoelectric crystal, more specifically, an output amplitude of the SEE output signal over a period of ADC acquisitions (samples), wherein the data is obtained by the acoustic emissions crystal self-test circuit introduced in FIG. 1 and acoustic emissions crystal is configured in an open circuit.

In a second experiment, the acoustic emissions crystal self-test circuit 100 applied a single 10 us pulse to the acoustic emission crystal 110. The acoustic emission crystal 110 is placed into an open circuit. The term open circuit refers to a condition where the acoustic emission crystal 110 is disconnected from the analogue acquisition circuitry 100. The system recorded the output amplitude of each of a series of data points, wherein each data point was taken in conjunction with a linear time spatial relation. The data is measured, recorded and subsequently charted on an analogue time plot 400 as illustrated in FIG. 5. Similar to the analogue time plot 300, the analogue time plot 400 also presents data along a sample number axis 312 and cross-referenced to an amplitude axis 314. The SEE sample 410 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude between 0 and 50.

It is noted that the low 10 us pulse results in similar outputs, and is therefore considered to be a nominal test configuration for evaluating the attachment of the acoustic emission crystal 110 to the bearing, bearing housing, or machine.

Figure 6:
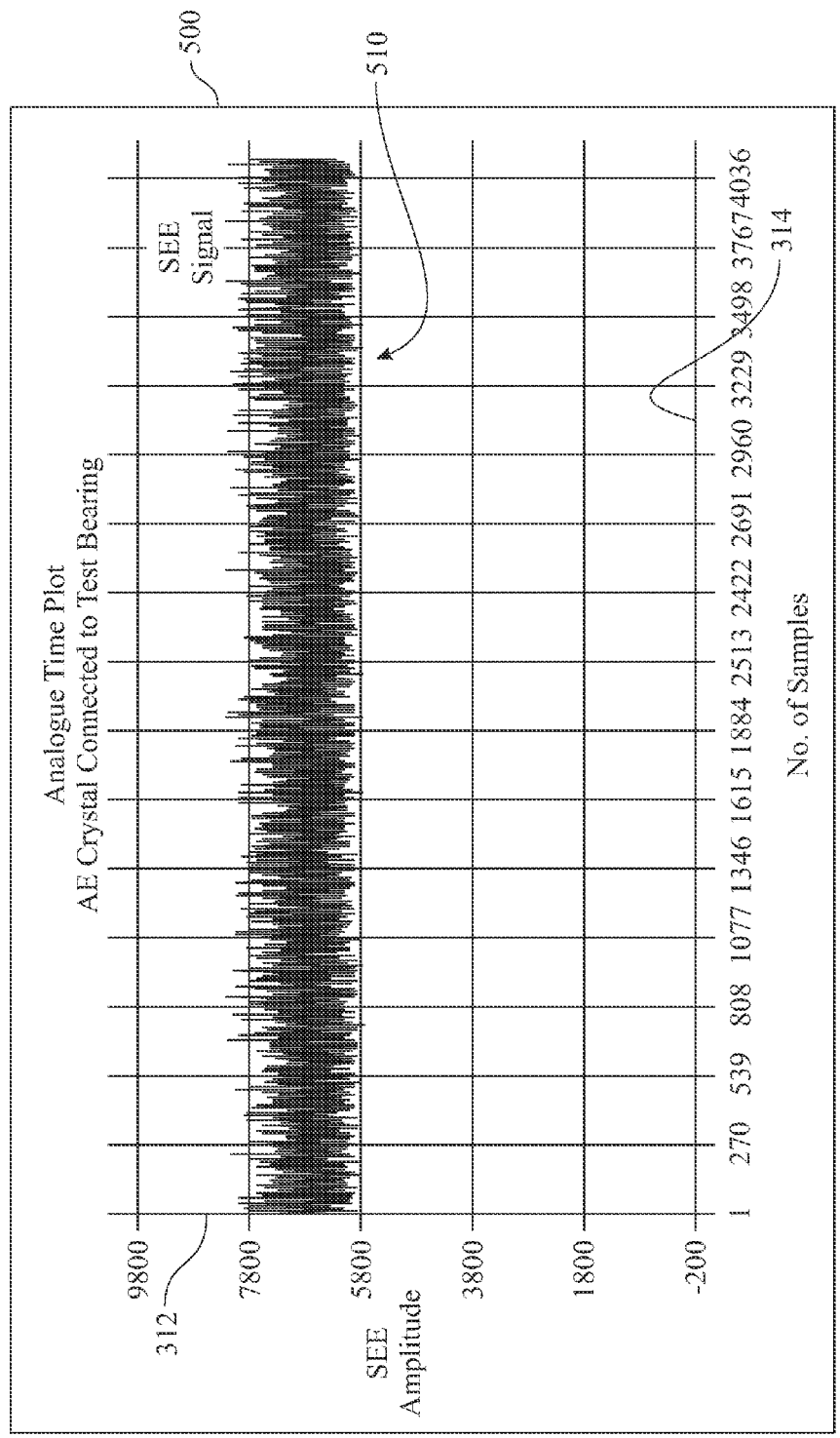
FIG. 6 presents an exemplary data chart illustrating an output signal of the SEE piezoelectric crystal, more specifically, an output amplitude of the SEE output signal over a period of ADC acquisitions (samples), wherein the acoustic emissions crystal is connected to a test bearing.

In a third experiment, the acoustic emissions crystal self-test circuit 100 applied a single 480 us pulse to the acoustic emission crystal 110. The acoustic emission crystal 110 is coupled to a test bearing in accordance with a standard coupling or attachment procedure. The system recorded the output amplitude of each of a series of data points, wherein each data point was taken in conjunction with a linear time spatial relation. The data is measured, recorded and subsequently charted on an analogue time plot 500 as illustrated in FIG. 6. Similar to the analogue time plot 300, 400, the analogue time plot 500 also presents data along a sample number axis 312 and cross-referenced to an amplitude axis 314. The SEE sample 510 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude between 5800 and 8000, with an average being approximately 6500.

Figure 7:
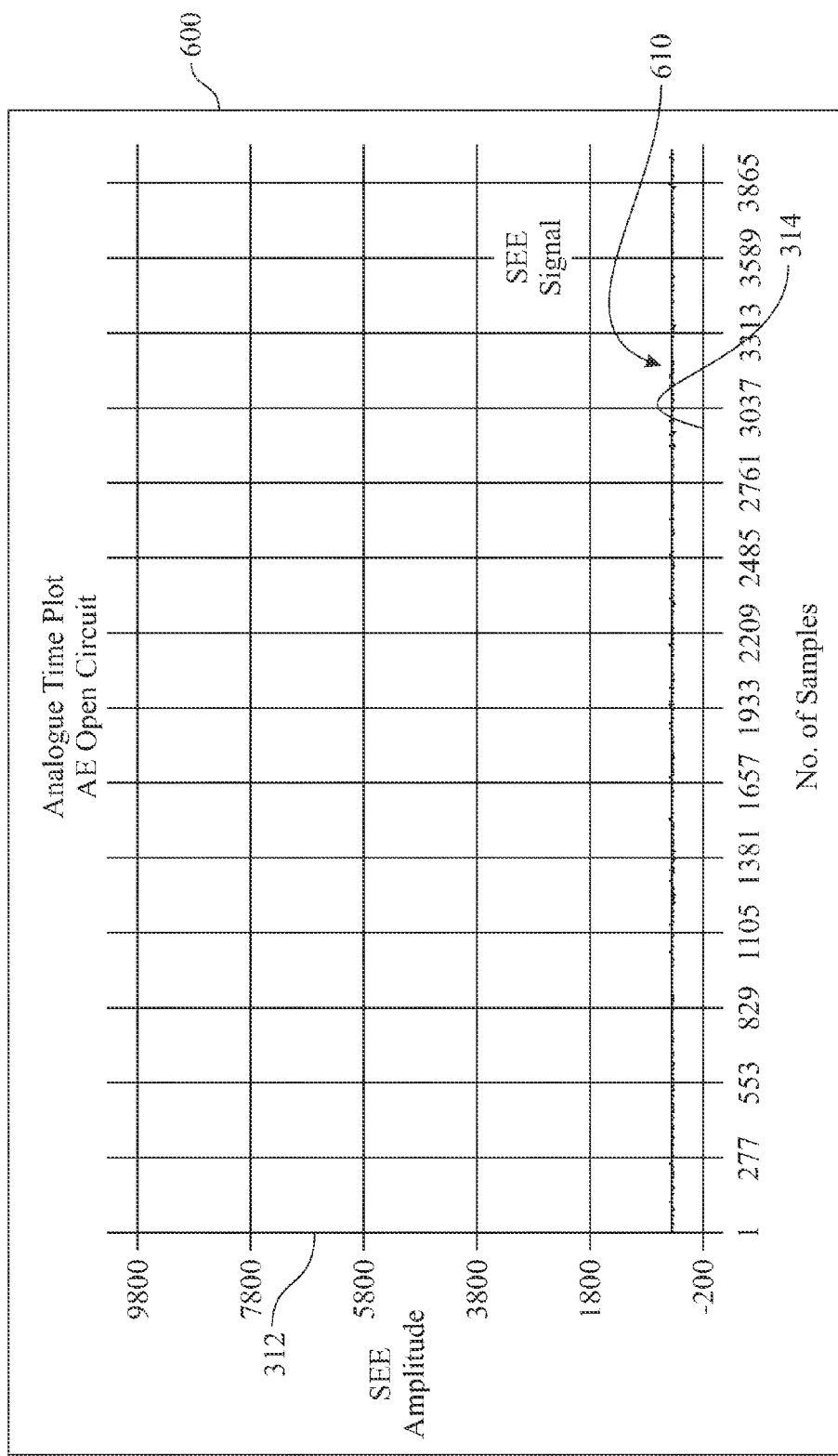
FIG. 7 presents an exemplary data chart illustrating an output signal of the SEE piezoelectric crystal, more specifically, an output amplitude of the SEE output signal over a period of ADC acquisitions (samples), wherein the acoustic emissions crystal is configured in an open circuit.

In a fourth experiment, the acoustic emissions crystal self-test circuit 100 applied a single 480 us pulse to the acoustic emission crystal 110. The acoustic emission crystal 110 is placed into an open circuit. The term open circuit refers to a condition where the acoustic emission crystal 110 is disconnected from the analogue acquisition circuitry 100. The system recorded the output amplitude of each of a series of data points, wherein each data point was taken in conjunction with a linear time spatial relation. The data is measured, recorded and subsequently charted on an analogue time plot 600 as illustrated in FIG. 7. Similar to the analogue time plot 300, 400, 500, the analogue time plot 600 also presents data along a sample number axis 312 and cross-referenced to an amplitude axis 314. The SEE sample 610 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude fluctuating around and slightly above zero, with an average being approximately 600.

Figure 8:
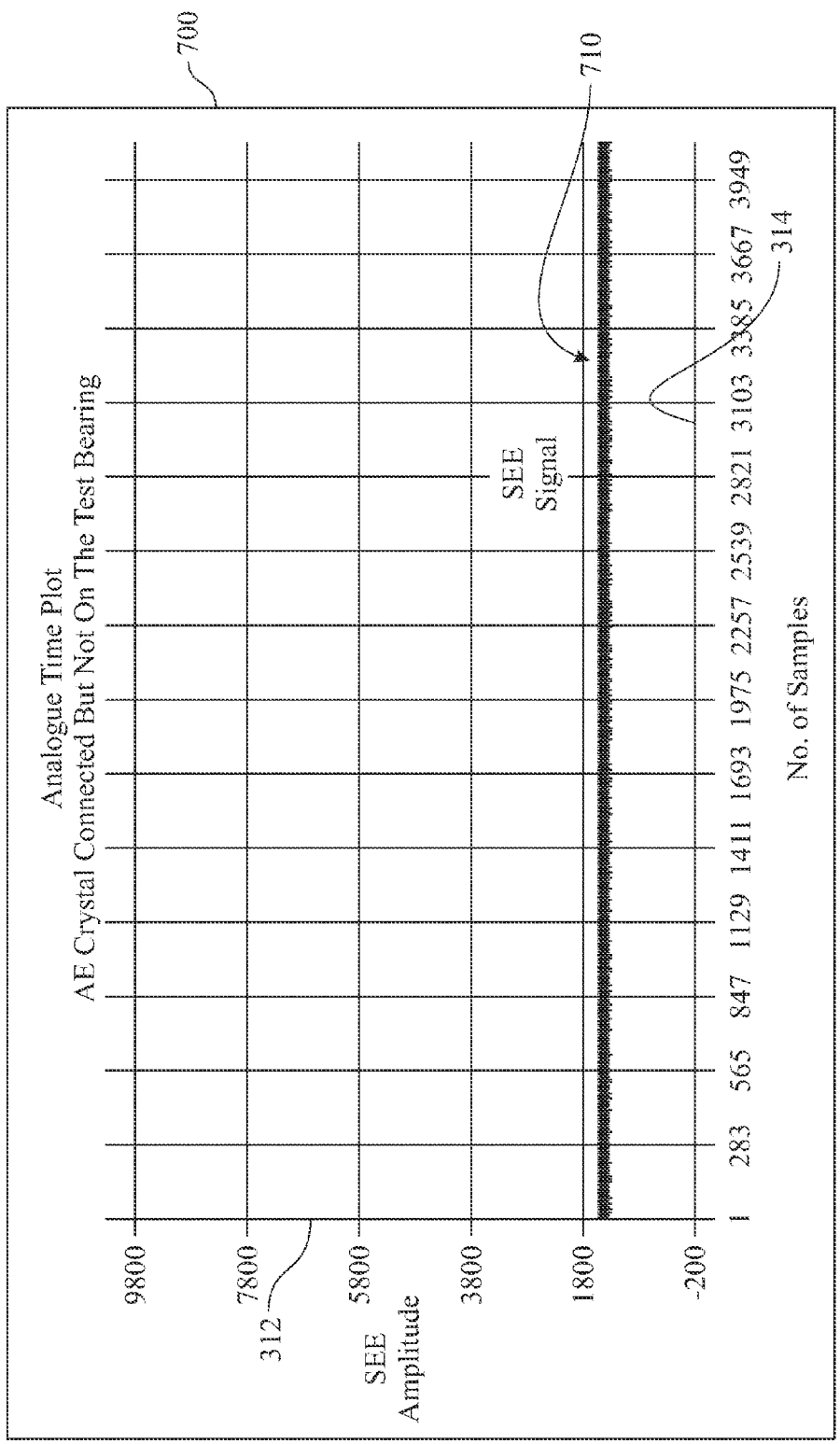
FIG. 8 presents an exemplary data chart illustrating an output signal of the SEE piezoelectric crystal, more specifically, an output amplitude of the SEE output signal over a period of ADC acquisitions (samples), wherein the acoustic emissions crystal is connected, but not on the test bearing.

In a fifth experiment, the acoustic emissions crystal self-test circuit 100 applied a single 480 us pulse to the acoustic emission crystal 110. The acoustic emission crystal 110 is connected to the circuit, but not attached to the test bearing. The system recorded the output amplitude of each of a series of data points, wherein each data point was taken in conjunction with a linear time spatial relation. The data is measured, recorded and subsequently charted on an analogue time plot 700 as illustrated in FIG. 8. Similar to the analogue time plot 300, 400, 500, 600 the analogue time plot 700 also presents data along a sample number axis 312 and cross-referenced to an amplitude axis 314. The SEE sample 710 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude between 1300 and 1700, with an average being approximately 1400.

It is noted that the 480 us pulse results in distinctly different outputs, and is therefore considered to be an acceptable test configuration for evaluating the attachment of the acoustic emission crystal 110 to the bearing, bearing housing, or machine.

Figure 9:
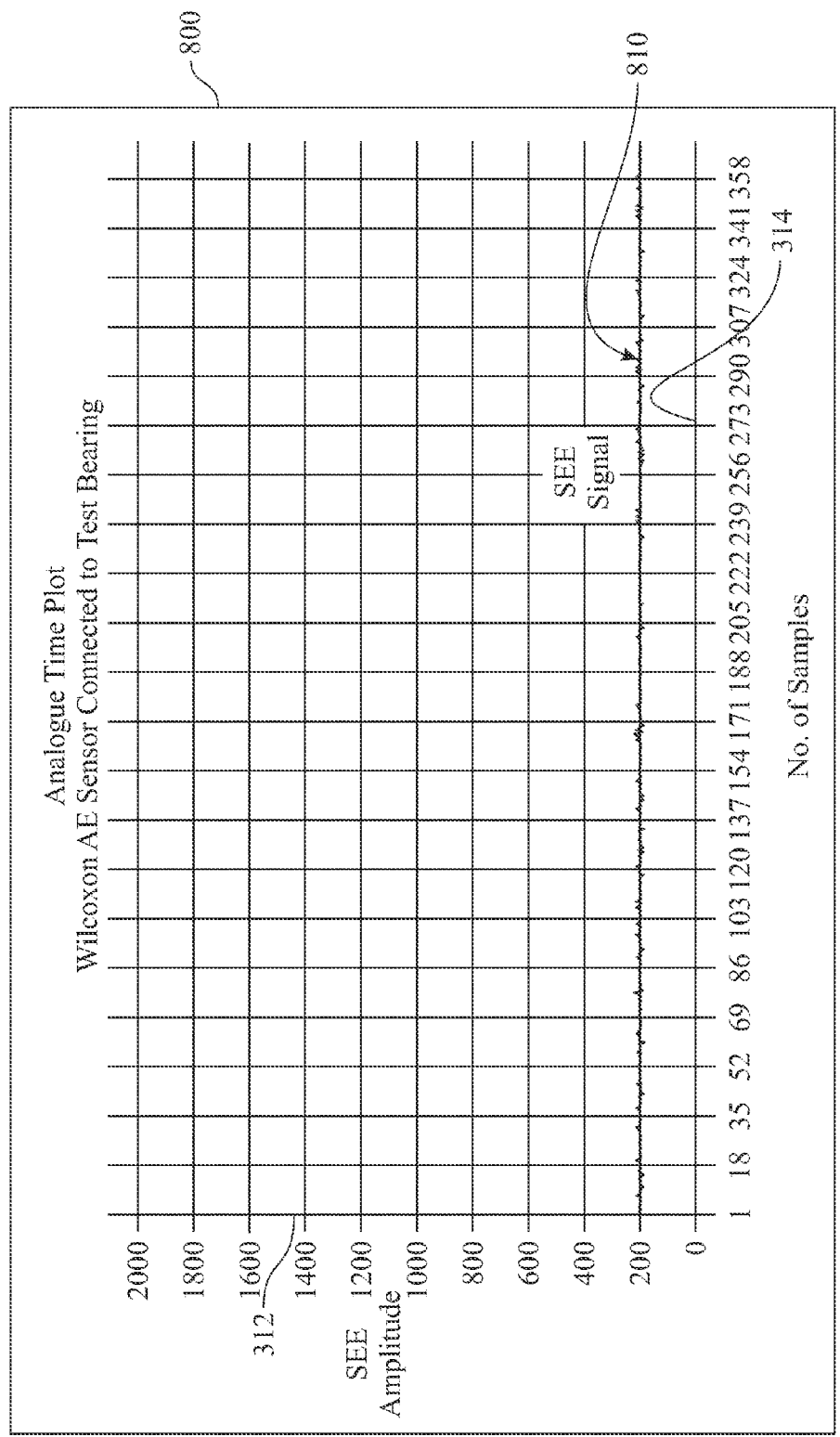
FIG. 9 presents an exemplary data chart illustrating an output signal of the SEE piezoelectric crystal, more specifically, an output amplitude of the SEE output signal over a period of ADC acquisitions (samples), wherein the samples are taken using a Wilcoxon acoustic emissions sensor connected to the test bearing.
Figure 10:
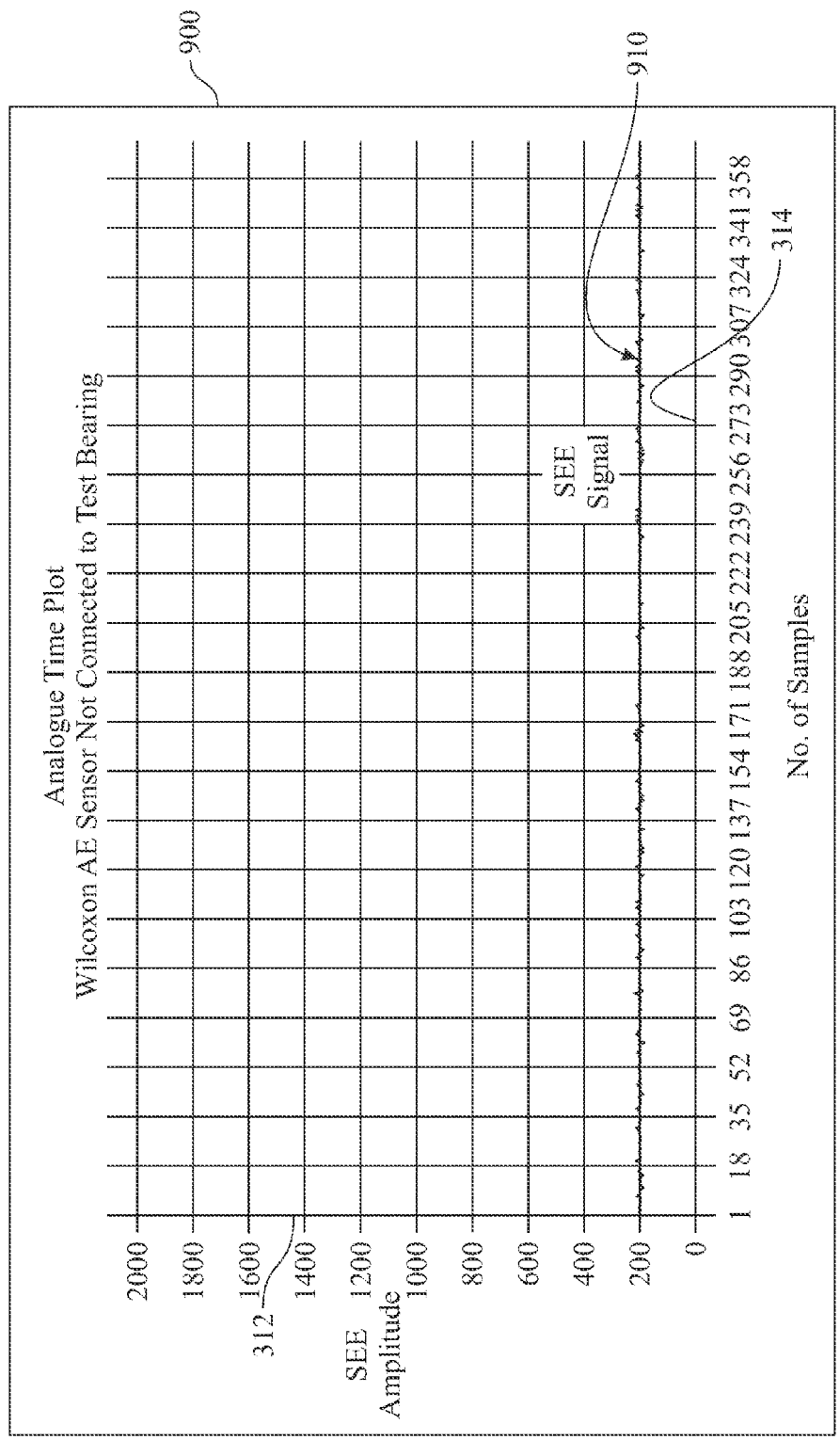
FIG. 10 presents an exemplary data chart illustrating an output signal of the SEE piezoelectric crystal, more specifically, an output amplitude of the SEE output signal over a period of ADC acquisitions (samples), wherein the samples are taken using a Wilcoxon acoustic emissions sensor that is not connected to the test bearing.
Figure 11:
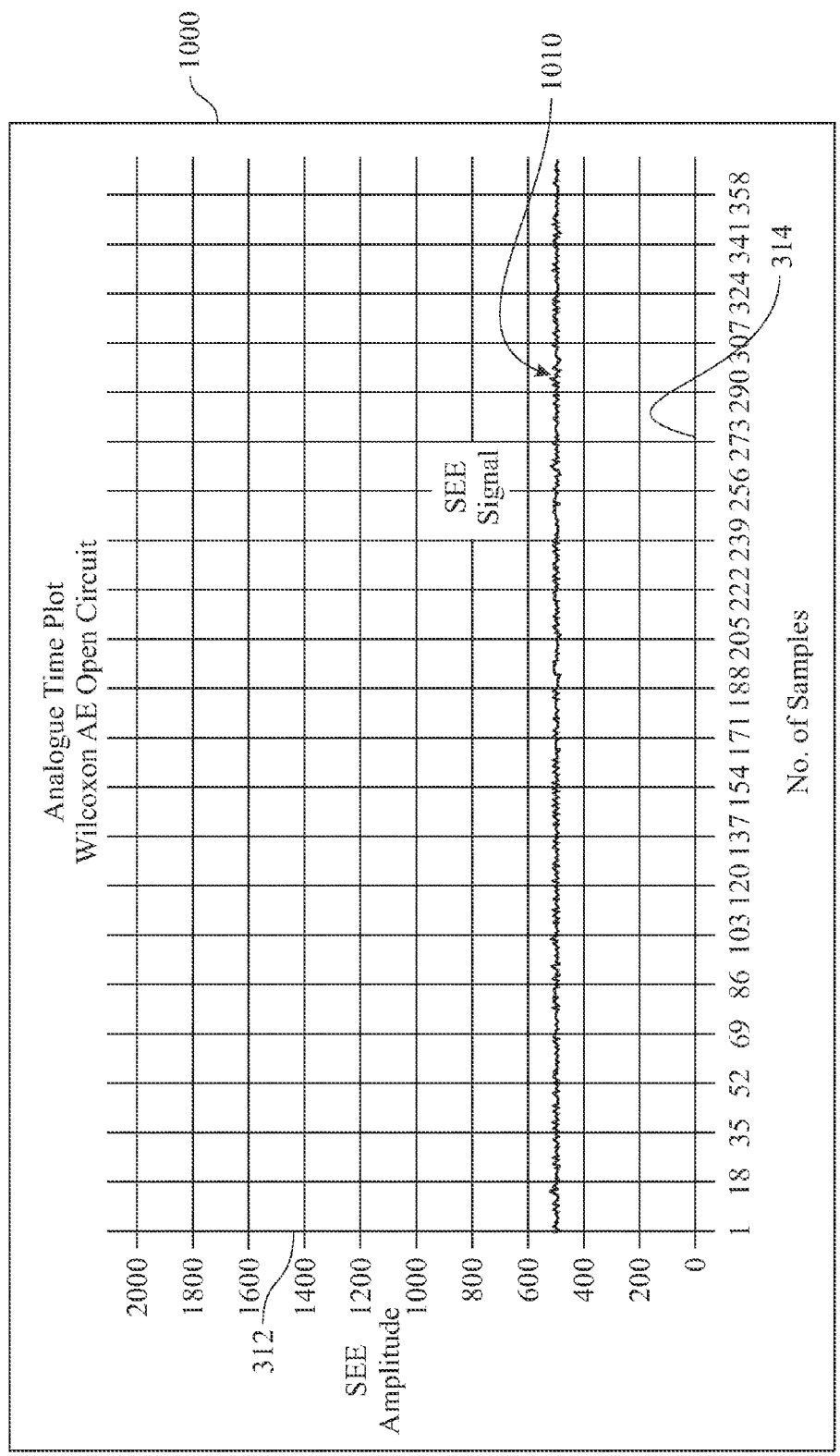
FIG. 11 presents an exemplary data chart illustrating an output signal of the SEE piezoelectric crystal, more specifically, an output amplitude of the SEE output signal over a period of ADC acquisitions (samples), wherein the samples are taken using a Wilcoxon acoustic emissions sensor that is configured in an open circuit.

A similar test was conducted using a Wilconxon SEE sensor, wherein the output is illustrated in the charts presented in FIGS. 9 through 11.

In a sixth experiment, the acoustic emissions crystal self-test circuit 100 applied a single 480 us pulse to the acoustic emission crystal 110. The acoustic emission crystal 110 is coupled to a test bearing in accordance with a standard coupling or attachment procedure. The system recorded the output amplitude of each of a series of data points, wherein each data point was taken in conjunction with a linear time spatial relation. The data is measured, recorded and subsequently charted on an analogue time plot 800 as illustrated in FIG. 9. Similar to the analogue time plot 300, 400, 500, 600, 700, the analogue time plot 800 also presents data along a sample number axis 312 and cross-referenced to an amplitude axis 314. The SEE sample 810 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude of approximately 200.

In a seventh experiment, the acoustic emissions crystal self-test circuit 100 applied a single 480 us pulse to the acoustic emission crystal 110. The acoustic emission crystal 110 is placed into an open circuit. The term open circuit refers to a condition where the acoustic emission crystal 110 is disconnected from the analogue acquisition circuitry 100. The system recorded the output amplitude of each of a series of data points, wherein each data point was taken in conjunction with a linear time spatial relation. The data is measured, recorded and subsequently charted on an analogue time plot 900 as illustrated in FIG. 10. Similar to the analogue time plot 300, 400, 500, 600, 700, 800, the analogue time plot 800 also presents data along a sample number axis 312 and cross-referenced to an amplitude axis 314. A SEE sample 910 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude of approximately 200.

In an eighth experiment, the acoustic emissions crystal self-test circuit 100 applied a single 480 us pulse to the acoustic emission crystal 110. The acoustic emission crystal 110 is connected to the circuit, but not attached to the test bearing. The system recorded the output amplitude of each of a series of data points, wherein each data point was taken in conjunction with a linear time spatial relation. The data is measured, recorded and subsequently charted on an analogue time plot 1000 as illustrated in FIG. 11. Similar to the analogue time plot 300, 400, 500, 600, 700, 800, 900, the analogue time plot 1000 also presents data along a sample number axis 312 and cross-referenced to an amplitude axis 314. A SEE sample 1010 presents the series of data points, wherein the data points are charted referencing an amplitude of the output of the acoustic emission crystal 110 obtained in a series of measurements over a period of time. The time period between samples is consistent. The output of the acoustic emissions crystal self-test circuit 100 has a general amplitude of approximately 500.

Although the differences are not as significant as the third through fifth experiments, the sixth through eighth experiments still present support for the utilization of the acoustic emissions crystal self-test circuit 100 as a suitable test process.

In summary, the acoustic emissions crystal self-test circuit 100 provides a significant benefit when testing an embedded acoustic emission crystal 110. The acoustic emissions crystal self-test circuit 100 can detect whether the acoustic emission crystal 110 is connected, disconnected from the bearing, or completely disconnected from the analogue acquisition circuitry 100. The data supports the benefits where the installation of the acoustic emission crystal 110 can be verified using the acoustic emissions crystal self-test circuit 100, which eliminates a need for use of a separate crystal or embedded crystal with a signal generator, or a requirement for exciting the bearing, bearing holder, or machine by tapping it with a metallic object.

The experimentation suggests the results of the vibration crystal self-test circuit 200 would be similar to the results of the acoustic emissions crystal self-test circuit 100. It is understood that the time period of the applied pulse may be adjusted for the application to obtain suitable self-test results.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

| Ref. No. | Description |
| --- | --- |
| 100 | acoustic emissions crystal self-test circuit |
| 102 | circuit controller |
| 110 | acoustic emission crystal |
| 120 | multiplexer IC |
| 122 | crystal self-test input |
| 124 | pre-amp gain |
| 126 | signal output |
| 130 | acoustic emission crystal acquired signal amplifier |
| 150 | bearing |

-continued

| Ref. No. | Description |
| --- | --- |
| 152 | bearing inner ring |
| 154 | bearing outer ring |
| 160 | bearing housing |
| 170 | machine housing |
| 200 | vibration crystal self-test circuit |
| 202 | circuit controller |
| 211 | vibration crystal |
| 220 | multiplexer IC |
| 222 | crystal self-test input |
| 224 | pre-amp gain |
| 226 | signal output |
| 231 | vibration crystal acquired signal amplifier |
| 250 | bearing |
| 252 | bearing inner ring |
| 254 | bearing outer ring |
| 260 | bearing housing |
| 270 | machine housing |
| 300 | analogue time plot |
| 310 | SEE sample |
| 312 | sample number axis |
| 314 | amplitude axis |
| 400 | analogue time plot |
| 410 | SEE sample |
| 500 | analogue time plot |
| 510 | SEE sample |
| 600 | analogue time plot |
| 610 | SEE sample |
| 700 | analogue time plot |
| 710 | SEE sample |
| 800 | analogue time plot |
| 810 | SEE sample |
| 900 | analogue time plot |
| 910 | SEE sample |
| 1000 | analogue time plot |
| 1010 | SEE sample |

What is claimed is:

1. A self-test circuit for testing a sensing emission crystal, the self-test circuit comprising:
   a voltage source;
   a ground;
   a controller;
   pulse waveform input;
   an analyzer; and
   a multiplexer IC having:
      a voltage input pin provided in signal communication with said ground,
      a ground pin provided in signal communication with said ground,
      a controller input pin provided in signal communication with said controller,
      a normally open pin provided in signal communication with said pulse waveform input,
      a common pin provided in signal communication with said sensing emission crystal;
      a normally closed pin output in signal communication with said analyzer,
   wherein in operation:
      said sensing emission crystal is installed and coupled to a component on a machine,
      a self-test is initiated, wherein said self-test steps are performed prior to a measurement of said machine under test,
      said pulse waveform input provides a waveform to said multiplexer IC,
      the controller configures said multiplexer IC to apply said waveform to said sensing emission crystal, wherein said waveform is provided in signal communication with said sensing emission crystal, adjusting a time prior for injection of an input signal to said sensing emission crystal, the waveform excites said sensing emission crystal, and the analyzer determines if said sensing emission crystal is correctly installed in said machine by passing said waveform emitted from said sensing emission crystal to said analyzer.

2. The self-test circuit for testing a sensing emission crystal as recited in claim 1, further comprising an acoustic emission crystal acquired signal amplifier, wherein said acoustic emission crystal acquired signal amplifier is integrated between said normally closed pin and said analyzer.

3. The self-test circuit for testing a sensing emission crystal as recited in claim 2, further comprising a square wave generator providing a square waveform for said pulse waveform input.

4. The self-test circuit for testing a sensing emission crystal as recited in claim 1, further comprising a square wave generator providing a square waveform for said pulse waveform input.

5. A self-test circuit for testing a sensing emission crystal, the self-test circuit comprising:
said sensing emission crystal attached to one of:
a bearing,
a bearing housing, and
a machine body retaining a bearing;
a voltage source;
a ground;
a controller;
a pulse waveform input;
an analyzer; and
a multiplexer IC having:
a voltage input pin provided in signal communication with said ground,
a ground pin provided in signal communication with said ground,
a controller input pin provided in signal communication with said controller,
a normally open pin provided in signal communication with said pulse waveform input,
a common pin provided in signal communication with said sensing emission crystal;
a normally closed pin output in signal communication with said analyzer,
wherein in operation:
said sensing emission crystal is installed and coupled to a component on the machine bod,
a self-test is initiated, wherein said self-test steps are performed prior to a measurement of said machine under test,
said pulse waveform input provides a waveform to said multiplexer IC,
the controller configures said multiplexer IC to pass said waveform to said sensing emission crystal, wherein said waveform is provided in signal communication with said sensing emission crystal, adjusting a time prior for injection of an input signal to said sensing emission crystal, the waveform excites said sensing emission crystal, and the analyzer determines if said sensing emission crystal is correctly installed in said machine by passing said waveform emitted from said sensing emission crystal to said analyzer.

6. The self-test circuit for testing a sensing emission crystal as recited in claim 5, further comprising an acoustic emission crystal acquired signal amplifier, wherein said acoustic emission crystal acquired signal amplifier is integrated between said normally closed pin and said analyzer.

7. The self-test circuit for testing a sensing emission crystal as recited in claim 6, further comprising a square wave generator providing a square waveform for said pulse waveform input.

8. The self-test circuit for testing a sensing emission crystal as recited in claim 5, further comprising a square wave generator providing a square waveform for said pulse waveform input.

9. A method of testing a sensing emission crystal, the method comprising steps of:
installing said sensing emission crystal in and coupling said sensing emission crystal to a machine,
configuring a multiplexer into a pulse injection configuration, placing a signal generation source in signal communication with said sensing emission crystal;
initiating a self-test is, wherein said self-test steps are performed prior to a measurement of said machine under test,
adjusting a time prior for injection of an input signal to said sensing emission crystal,
injecting a waveform into said sensing emission crystal;
configuring said multiplexer into a signal collection configuration, placing a signal generation source in signal communication with a signal analyzer;
obtaining a waveform output from said sensing emission crystal;
providing said waveform output to a signal analyzer; and
determining if said sensing emission crystal is correctly installed in said machine based upon said waveform output.

10. The method of testing a sensing emission crystal as recited in claim 9, wherein the step of injecting said waveform into said acoustic emissions crystal injects a square waveform.

11. The method of testing a sensing emission crystal as recited in claim 10, further comprising a step of amplifying said waveform output prior to said step of providing said waveform output to a signal analyzer.

12. The method of testing a sensing emission crystal as recited in claim 9, further comprising a step of amplifying said waveform output prior to said step of providing said waveform output to a signal analyzer.

* * * * *